United States Patent
Lee et al.

(10) Patent No.: US 9,903,834 B2
(45) Date of Patent: Feb. 27, 2018

(54) FET TYPE GAS-SENSITIVE DEVICE HAVING HORIZONTAL FLOATING GATE

(71) Applicant: Seoul National University R&DB FOUNDATION, Seoul (KR)

(72) Inventors: Jong-Ho Lee, Seoul (KR); Chang-Hee Kim, Daegu (KR)

(73) Assignee: Seoul National University R&DB Foundation, Seoul (KR)

( * ) Notice: Subject to any disclaimer, the term of this patent is extended or adjusted under 35 U.S.C. 154(b) by 3 days.

(21) Appl. No.: 14/073,091

(22) Filed: Nov. 6, 2013

(65) Prior Publication Data

US 2014/0131774 A1    May 15, 2014

(30) Foreign Application Priority Data

Nov. 9, 2012    (KR) .................. 10-2012-0126853

(51) Int. Cl.
*G01N 27/403*    (2006.01)
*G01N 27/414*    (2006.01)

(52) U.S. Cl.
CPC .................. *G01N 27/4143* (2013.01)

(58) Field of Classification Search
CPC ............ G01N 27/414; G01N 27/4141; G01N 27/4143; G01N 27/4148; G01N 27/14; H01L 29/66825
USPC ....................................................... 257/253
See application file for complete search history.

(56) References Cited

U.S. PATENT DOCUMENTS

| | | | |
|---|---|---|---|
| 4,849,798 A | | 7/1989 | Watanabe |
| 5,767,549 A | * | 6/1998 | Chen et al. ................... 257/347 |
| 6,111,280 A | * | 8/2000 | Gardner et al. .............. 257/253 |
| 7,772,617 B2 | | 8/2010 | Fleischer et al. |
| 2003/0010119 A1 | * | 1/2003 | Toyoda ...................... 73/335.04 |
| 2008/0121946 A1 | * | 5/2008 | Youn .................... G01N 27/127 |
| | | | 257/253 |

OTHER PUBLICATIONS

Barranca et al.—"Using a Floating-Gage MOS Transistor as a Transducer in a MEMS Gas Sensing System"—Sensors 2010, 10, pp. 10413-10434.

* cited by examiner

*Primary Examiner* — Thao X Le
*Assistant Examiner* — Laura Dykes
(74) *Attorney, Agent, or Firm* — Gerald E. Hespos; Michael J. Porco; Matthew T. Hespos

(57) ABSTRACT

A FET type gas-sensitive device has a floating electrode formed in a horizontal direction. The device achieves noise reduction, process simplification, pollution control, sensing speed improvement, various sensing material applicability and mechanical stability etc. in comparison with a gas-sensitive device that is vertically stacked with a floating electrode, a sensing material layer and a control electrode. The device can be assembled easily with a plurality of gas-sensitive devices being operated by various sensing mechanisms in one substrate.

20 Claims, 14 Drawing Sheets

FET TYPE GAS-SENSITIVE DEVICE HAVING HORIZONTAL FLOATING GATE

CROSS-REFERENCE TO RELATED APPLICATION

This application claims priority to Korean Patent Application No. 10-2012-0126853, filed on Nov. 9, 2012, under 35 U.S.C. 119, the entire contents of which are hereby incorporated by reference.

BACKGROUND OF INVENTION

1. Field of the Invention

The present invention relates to gas-sensitive sensors, and more particularly to a metal oxide semiconductor field effect transistor's (MOSFET's) FET type gas-sensitive device having a horizontal floating gate for solving problems of the conventional sensor having a vertically formed gate and sensing layer and for being used in fabricating chemical sensors and biosensors etc.

2. Description of the Related Art

Recently, in order to sense chemical and bio materials, various structural sensors are being developed. Among these sensors, field effect transistors (FETs) having a floating gate are being studied due to having a high input impedance and a high amplification factor. Particularly, because of the needs of a low power, a high sensitivity induced by a high transconductance and a convergence fused with the conventional CMOS circuit, the research on FET type sensors is gradually increasing.

In the conventional study, it is mainly embodied to have a structure that a floating gate and a sensing layer are vertically formed. Main fabrication process of the conventional structures includes forming a gate insulating layer on a silicon substrate, forming a sensing layer on a top surface of the gate insulating layer and forming a control electrode on the sensing layer. The sensing principle is that, before and after sensing, some effects such as a capacitance change, a work function change and a charge generation/extinction appear in a sensing layer, some effects induce a potential change in a channel and, finally, the potential change induces a drain electric current change. The drain current change is read to judge gas-sensitivity and to quantitatively express the degree of sensing.

By reviewing the conventional publication documents cited below, we can see the following: U.S. Pat. No. 4,849,798 (hereinafter referred to as Patent document 1) shows a typical vertical shaped structure that includes a floating electrode formed on a gate insulating layer, a sensing layer on the top surface of the floating electrode and a control electrode on the top surface of the sensing layer. This structure is useful as a method for sensing a drain current by measuring a capacitance change of a sensing layer before and after sensing. In the device structure of Patent document 1, because the sensing layer is formed between the vertically formed insulator and control electrode, the reactants are permeated into a side wall to cause the reaction. But because a gate region (defining a width and a length of a channel) of FET used in the sensor has a large size generally, the reaction speed is slow. Thus, it takes too much time to react by a long permeated length from the side wall and it also spends a vast time in removing the permeated gas. For reducing the reaction time, the gate size must be decreased as much as possible. However, it needs expensive apparatuses to reduce the gate area in a current semiconductor process. Thus, it causes a cost increasing problem. In order to solve the problem, a structure using a porous metal as the control electrode to react gas particles to the sensing material via the control electrode and another structure using a control electrode as the sensing material are developed as gas sensors, but the kind of gas being able to sense is limited. Because only one material is used to form the insulating layer in the fabrication process, it is difficult to sense various gases. And this structure, as mentioned above, is a vertical shape using a capacitance change before and after sensing. Thus, if the sensing layer is an insulating material, the electrode can be formed on the sensing layer. If the sensing layer is a semiconductor material, it needs processes for forming an insulating layer and an electrode. In this case, it has a problem to cause physical and chemical damages on the sensing layer during the electrode and insulating layer forming processes. And most MOSFET type sensors are covered with a thick passivation layer for solving a reliability problem induced by the exterior environmental exposure. In Patent document 1, the passivation layer is formed just above the gate insulating layer to form a thick gate insulating layer. Thus, the coupling ratio of the control electrode is reduced and it comes to fall the sensitivity of the sensor.

In U.S. Pat. No. 7,772,617 (hereinafter referred to as Patent document 2), it shows a structure having an air layer between a sensing layer and a floating gate. In this structure, the sensing layer plays a role of a control electrode. After sensing, a work function change of the sensing layer and a FET threshold voltage is consequently changed to induce a drain current change as a principle of a sensor. This sensor structure has an air layer for solving the problem that the device reaction time is determined depending on the size of the gate described in Patent document 1. The air layer forming process includes forming a sacrificial layer between a floating gate and a sensing layer and forming the air layer by etching the sacrificial layer isotropically. However, because of the air layer with a small dielectric constant, a coupling ratio between the control electrode and the floating electrode is decreased and it comes to reduce the sensitivity of a sensor. In order to solve the problem, the area between the control electrode and the floating electrode has to be increased. But when the area is increased, there are other problems. First, when the area of a sensor is increased, the number of sensors fabricated on one substrate is reduced and the fabricating cost is increased. Second, the conventional MOSFET type gas sensors mainly use the sensing materials based on a metal oxide. The sensing materials are mainly operated in high temperature. If the area of a sensor broadens, the area of a sensing layer region also broadens. Because the more heat energy has to be transferred into the sensing layer, the electric power consumption is increased. Third, when the sacrificial layer is isotropically etched using an etching solution, there is a problem the insulating layer (i.e., passivation layer) protecting the sensing layer and the active region is exposed in the etching solution for a long time. Accordingly, there is a selection limit of materials for forming the sensing layer that does not nearly react with the etching solution removing the sacrificial layer. And a thick passivation layer has to be formed to protect the active region. Bur if the thickness of the passivation layer is increased, the coupling ratio between the control electrode and the floating electrode is reduced.

In addition, for fabricating the sensor of Patent document 2, at least 6 masks are needed and it makes to increase the process complexity and to generate a difficulty in the predetermined fabrication process step. Thus, the yield is reduced and the fabricating cost of a sensor is increased.

In the sensor introduced in a paper, Mario Alfredo Reyes Barranca et al., "Using a Floating-Gate MOS Transistor as a Transducer in a MEMS Gas Sensing System," Sensors 2010, 10, 10413-10434 (hereinafter referred to as Non-patent document 1), when the sensing material reacts to gas, charges are induced in the floating electrode and have influence on a drain current. In this device structure, a sensing region and a control electrode are equipped together on a floating electrode and it is a sensor using the effect of a charge generation/extinction depending on before and after the gas reaction in a sensing material. In the structure, if a sensing material is reacted to gas, net charges are generated in the sensing material and the net charges induce again charges in the floating electrode located the below. The induced charges change the potential of the floating electrode and it comes to change a FET threshold voltage and to change a drain current. And under the sensing layer, a separate heater can be formed to transfer heat to the sensing layer. In this case, for protecting the heat transfer into an unwanted region, the silicon substrate is etched. In this structure, because the floating electrode must be widely formed, the parasite capacitance components are increased. And the important parts of the sensor can be damaged in the etching process of a silicon substrate.

Therefore, the development of devices having a new structure is needed to solve the problems in the conventional published devices.

SUMMARY OF THE INVENTION

The present invention is contrived to solve the problems of the conventional FET type sensors having vertically formed floating and control electrodes and a sensing layer: a selection limit of sensing material in the fabrication process, a low coupling ratio between the control and floating electrodes due to the parasite capacitance components, a low sensitivity and a high power consumption, and a high fabricating cost generated by a process complexity etc. And the present invention is also proposed to provide device structures having horizontally formed control and floating electrodes and a sensing material layer interlaid between the electrodes. In addition, based on the structures according to the present invention, some sensing mechanisms are provided and, in order to improve the sensing precision, some arrays can be embodied with a plurality of gas-sensitive devices operated by the sensing mechanisms.

The present invention provides the following sensor structures and characteristics as the means to solve the conventional problems.

A FET (field effect transistor) type gas-sensitive device according to the present invention can be comprised of: a semiconductor substrate; a semiconductor body formed to be protruded on the semiconductor substrate; a separating insulation layer formed on a side wall of the semiconductor body and on the semiconductor substrate; a gate insulating layer formed on the semiconductor body; a floating electrode formed on the gate insulating layer and on the separating insulation layer; a control electrode formed on the separating insulation layer to be face to face with and to be horizontally separated from at least one side wall of the floating electrode; a sensing material layer formed between the control electrode and the floating electrode; and source/drain regions formed in the semiconductor body at the both sides of the floating electrode.

A first insulating layer can be formed at least one of between the control electrode and the sensing material layer and between the floating electrode and the sensing material layer.

A passivation layer can be formed on the top surfaces of the floating electrode, the control electrode and the first insulating layer, and the sensing material layer can be formed to cover a part of the passivation layer.

The first insulating layer can be formed one of between the control electrode and the sensing material layer and between the floating electrode and the sensing material layer, and a first electrode can be formed the other of between the control electrode and the sensing material layer and between the floating electrode and the sensing material layer.

A passivation layer can be formed on the top surfaces of the floating electrode, the control electrode and the first insulating layer, the first electrode can be formed to cover a part of the passivation layer, and the sensing material layer can be formed to cover each part of the first electrode and the passivation layer.

A first electrode can be formed between the control electrode and the sensing material layer, and a second electrode can be formed between the floating electrode and the sensing material layer.

A first insulating layer can be formed at least one of between the control electrode and the first electrode and between the floating electrode and the second electrode.

A passivation layer can be formed on the top surfaces of the floating electrode, the control electrode and the first insulating layer, the first electrode can be formed to cover a part of the passivation layer formed on the top surface of the control electrode, the second electrode can be formed to cover a part of the passivation layer formed on the top surface of the floating electrode, and the sensing material layer can be formed between the first electrode and the second electrode to cover each part of the first electrode and the second electrode.

The sensing material layer can be formed on a passivation layer formed on the surface of a groove between the control electrode and the floating electrode.

The first electrode can be formed on the passivation layer between the control electrode and the sensing material layer.

The second electrode can be formed on the passivation layer between the floating electrode and the sensing material layer.

The semiconductor body can be doped with impurities to form a buried channel for improving signal-to-noise ratio (SNR) by reducing the noises and for improving carrier mobility.

The control electrode can be formed of one or more materials of polysilicon, polysilicon germanium, silicide, metal, conductive metal oxide and conductive nitride.

The sensing material layer can be formed of a material that reacts to a predetermined gas and results in a change of a dielectric constant or a generation or extinction of electric charges.

The first electrode can be formed between the control electrode and the sensing material layer and the sensing material layer can be formed of a material that reacts to a predetermined gas and results in a change of a work function of the control electrode or a change of a dielectric constant or a generation or extinction of electric charges.

The first and second electrodes can be formed of metals different from each other and the sensing material layer can be formed of a material that reacts to a predetermined gas and results in a change of an electromotive force between the first and second electrodes or a change of a dielectric constant or a generation or extinction of electric charges.

An air gap can be formed between the control electrode and the sensing material layer or between the sensing material layer and the floating electrode.

The air gap can be formed between the sensing material layer and the floating electrode and at least one of a first insulating layer and a first electrode can be further formed between the control electrode and the sensing material layer.

The floating electrode can have an uneven side wall facing to face with the control electrode and the control electrode can have an uneven side wall formed reversely to the uneven side wall of the floating electrode to form an interdigitated shape with the floating electrode.

The control electrode can further have an uneven side wall opposite to the side wall facing to face with the floating electrode to form a zigzag shape and is used as a heater. And it is possible to emit heat by a current flow of an electric power applied to two input terminals formed on both ends of the longitudinal direction of the control electrode.

In other words, the input terminals of the control electrode can be applied with a DC voltage or a pulse type voltage. In case of the latter, a heating voltage and a reading voltage can be combined and simultaneously applied to the input terminals of the control electrode.

The semiconductor substrate can be etched with a predetermined depth to form an air layer under the control electrode and the sensing material layer for reducing the loss of heat toward the substrate. Furthermore, the air layer can be extended to the semiconductor substrate located under a part of the floating electrode adjacent to the sensing material layer by further removing the part of the semiconductor substrate. By doing this, it enables to reduce parasite capacitance components for improving a coupling ratio between the control electrode and the floating electrode.

A FET type gas-sensitive device according to the present invention can be also comprised of: a semiconductor substrate; a semiconductor body formed to be protruded on the semiconductor substrate; a separating insulation layer formed on a side wall of the semiconductor body and on the semiconductor substrate; a gate insulating layer formed on the semiconductor body; a floating electrode formed on the gate insulating layer and on the separating insulation layer; a passivation layer formed on the floating electrode and on the separating insulation layer; a first electrode formed on the passivation layer to be face to face with and to be horizontally separated from at least one side wall of the floating electrode; a sensing material layer formed on the passivation layer between the first electrode and the floating electrode; and source/drain regions formed in the semiconductor body at the both sides of the floating electrode.

Here, a second electrode can be further formed on the passivation layer to cover a side wall and a partial top surface of the floating electrode facing to face with the first electrode and the sensing material layer can be formed between the first and second electrodes and on the passivation layer.

The second electrode can be electrically connected to the floating electrode through a contact hole formed on the passivation layer.

A gas-sensitive device array according to the present invention can be comprised of a plurality of gas-sensitive devices arrayed in a semiconductor substrate for sensing two or more different kinds of gases. Here, the plurality of gas-sensitive devices comprise two or more gas-sensitive devices having different operation mechanisms due to a different structure or sensing material and each of the gas-sensitive devices is a FET type gas-sensitive device mentioned above as the present invention.

The plurality of gas-sensitive devices can comprise gas-sensitive devices having two or more different operation mechanisms of a dielectric constant change, a generation or extinction of electric charges, a work function change and an electromotive force change of the sensing material layer.

The FET type gas-sensitive device according to the present invention enables to solve the problems of the structures introduced in the above mentioned Patent and Non-Patent documents by the horizontal formation of the control electrode, the floating electrode and the sensing material layer. Particularly, in the Patent document 1, the gas reaction time is slow due to the large size of the gate area (the width and length of the channel). But, in the present invention, because the reaction gas vertically infiltrates into the sensing material layer to attach and detach, it enables to vastly reduce the reaction time. And in the present invention, because the sensing material layer can be formed at the last step of the process, it is not damaged. Thus, it enables to improve the selectivity of the sensing materials, the protection from damage and the yield rate.

The FET type gas-sensitive device according to the present invention enables to have higher the sensitivity, lower the power consumption and greater the miniaturization than those of the sensor of Patent document 2 due to the high coupling ratio embodied by the interdigitated shape of the control electrode and the floating electrode. In the Non-patent document 1, the control electrode and the sensing material are separately formed on a floating electrode and it makes to broaden the area of the floating electrode and to increase the parasite capacitance components and to consequently reduce the sensitivity. However, in the present invention, the sensitivity of the device can be vastly improved because the control electrode and the floating electrode are horizontally formed for increasing the capacitance between the control electrode and the floating electrode and for reducing the parasite capacitance components included in the floating electrode.

The FET type gas-sensitive device according to the present invention enables to more increase the heat transfer efficiency than the conventional case using a thick insulation layer and to easily return the gas attached on the sensing material layer to the original detached state by using the control electrode as a heater and by configuring the control electrode and the sensing material layer to be separated with a thin insulating layer or to directly contact to each other.

The FET type gas-sensitive device according to the present invention enables to more minimize the loss of heat than the conventional sensor by forming an air layer in the semiconductor substrate adjusted to the sensing material layer by an isotropic etching to stop the transfer of the heat emitted from the control electrode to the substrate.

The FET type gas-sensitive device according to the present invention enables to improve the yield rate and to reduce the fabrication cost due to the simple fabrication process and the possibility of miniaturization in comparison with the conventional sensor.

The FET type gas-sensitive device and the gas-sensitive device array using the same according to the present invention enable to increase the sensing precision by using the operating and sensing mechanism of the capacitance change depending on the change of dielectric constants before and after the sensing, the work function change, the generation/extinction of electric charges and the electromotive force (EMF) change and to coincidentally sense two or more different gases by the array embodied in the same substrate with two or more gas-sensitive devices operated with the sensing mechanisms differing from each other.

BRIEF DESCRIPTION OF THE DRAWINGS

FIG. 1A is a top view, FIG. 1B is a cross-sectional view taken along line A-A' of FIG. 1A and FIG. 1C is a cross-sectional view taken along line B-B'.

FIG. 3A is a top view and FIG. 3B is a cross-sectional view taken along line A-A' of FIG. 3A.

FIG. 5A is a top view and FIGS. 5B and 5C are cross-sectional views taken along line A-A' of FIG. 5A to show each embodiment.

FIG. 7A is a top view and FIG. 7B is a cross-sectional view taken along line A-A' of FIG. 7A.

FIG. 9A is a top view and FIGS. 9B to 9E are cross-sectional views taken along line A-A' of FIG. 9A to show each embodiment.

FIG. 11A is a top view and FIG. 11B is a cross-sectional view taken along line A-A' of FIG. 11A.

FIG. 12A is a top view and FIG. 12B is a cross-sectional view taken along line A-A' of FIG. 12A.

FIG. 14A is a top view and FIG. 14B is a cross-sectional view taken along line A-A' of FIG. 14A.

FIG. 15A is a top view and FIG. 15B is a cross-sectional view taken along line A-A' of FIG. 15A.

FIG. 16A is a top view and FIG. 16B is a cross-sectional view taken along line A-A' of FIG. 16A.

FIG. 17A is a top view and FIG. 17B is a cross-sectional view taken along line A-A' of FIG. 17A.

FIG. 19A is a top view and FIG. 19B is a cross-sectional view taken along line A-A' of FIG. 19A.

FIG. 21A is a top view, FIG. 21B is a cross-sectional view taken along line A-A' of FIG. 21A and FIG. 21C is a cross-sectional view taken along line B-B' of FIG. 21A.

Figure 1A:
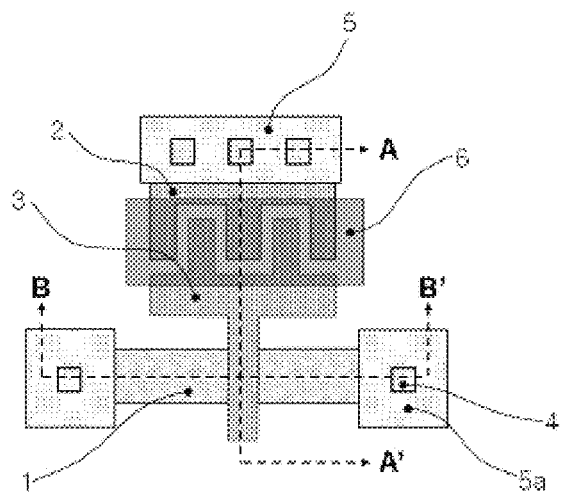
FIGS. 1A to 1C are showing a FET type gas-sensitive device having a horizontal floating gate enabling to sense the change of capacitance or the generation/extinction of electric charges according to one embodiment of the present invention.

In these drawings, the following reference numbers are used throughout: reference number 1 indicates an active region, 2 a control electrode, 3 a floating electrode, 4 a contact, 5 a first electrode, 5a a source/drain electrode, 6 a sensing material layer, 7 a semiconductor substrate, 8 a separating insulation layer, 9 a gate insulating layer, 10 a passivation layer, 11 a first insulating layer, 12 a semiconductor body, 13 a source/drain region, 14 a second electrode, 15 an air layer, 100 a gas-sensitive device sensing the change of capacitance of a sensing material layer, 200 a gas-sensitive device sensing the generation/extinction of electric charges of a sensing material layer, 300 a gas-sensitive device sensing the change of a work function of a sensing material layer and 400 a gas-sensitive device sensing the change of an electromotive force of a sensing material layer.

DETAILED DESCRIPTION OF THE PREFERRED EMBODIMENTS

Detailed descriptions of preferred embodiments of the present invention are provided below with reference to accompanying drawings.

A FET type gas-sensitive device according to a first embodiment of the present invention, as commonly shown in FIGS. 1A to 6, 9A to 10 and 14A to 21C, can be comprised of: a semiconductor substrate 7; a semiconductor body 12 formed to be protruded on the semiconductor substrate 7; a separating insulation layer 8 formed on a side wall of the semiconductor body 12 and on the semiconductor substrate 7; a gate insulating layer 9 formed on the semiconductor body 12; a floating electrode 3 formed on the gate insulating layer 9 and on the separating insulation layer 8; a control electrode 2 formed on the separating insulation layer 8 to be face to face with and to be horizontally separated from at least one side wall of the floating electrode 3; a sensing material layer 6 formed between the control electrode 2 and the floating electrode 3; and source/drain regions 13 formed in the semiconductor body 12 at the both sides of the floating electrode 3.

Here, the semiconductor body 12 is preferably doped with impurities in order that a buried channel can be formed inside and at a little distance from the surface of the semiconductor body 12 through controlling an impurity type, a doping concentration and a doping profile etc. By the buried channel, it is possible to reduce a noise of the device to increase the signal-to-noise ratio (SNR) which is a very important factor of the gas-sensitive sensor.

The control electrode 2 can be formed of one or more of impurity-doped polysilicon, polysilicon germanium, silicide, metal, conductive metal oxide and conductive nitride.

And the sensing material layer 6 can be directly filled between the control electrode 2 and the floating electrode 3 being face to face with and horizontally separated from each other or, as the below mentioned embodiments, can be filled on an extra insulating or conductive material firstly interposed between them.

Particularly, if the sensing material layer 6 is formed of a material that reacts to a predetermined gas and results in a change of a dielectric constant or a generation or extinction of electric charges, it enables to induce the change of capacitance between the control electrode 2 and the floating electrode 3 or to directly make an effect on the electric potential of the floating electrode 3. By doing this, a difference between the operating voltage applied to the control electrode 2 and the voltage transferred to the floating electrode 3 is developed by depending on whether the gas exists or not and consequently has an effect on the channel formation and/or the channel resistance of the semiconductor body 12. Therefore, it is possible to detect a predetermined gas by sensing electric currents flowing through source/drain electrodes 5a using the above operating mechanism.

And in the composition of the first embodiment, because the control electrode 2, the floating electrode 3 and the sensing material layer 6 are basically formed in a horizontal direction, it enables to solve the problems of the conventional vertical type gas-sensitive device. Especially, in comparison with the above mentioned Patent document 1 which shows a slow gas reaction time due to the large size of the gate area (determining the width and length of the channel), it is possible to vastly reduce the reaction time by enabling the reaction gas to vertically infiltrate into the sensing material layer 6 and to be attached or detached in the first embodiment of the present invention.

Figure 1B:
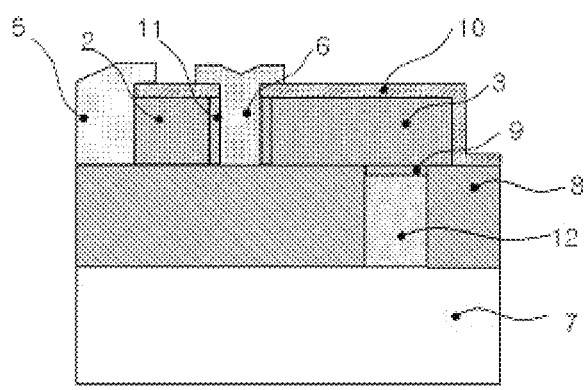
Figure 1C:
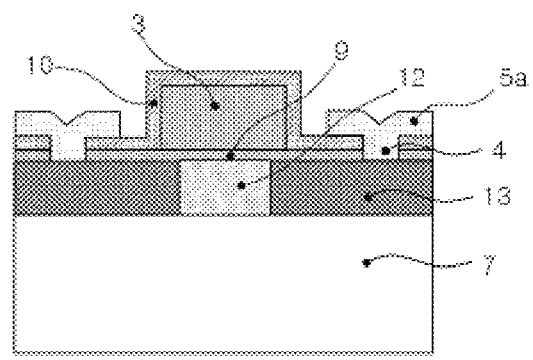
Figure 2:
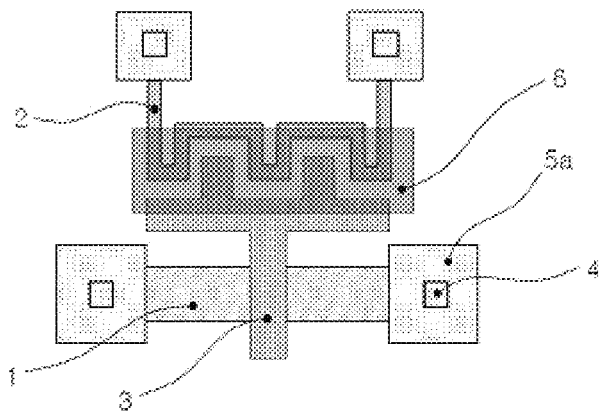
FIG. 2 is a modified view of a gas-sensitive device shown in FIG. 1A and is showing one example of a heater embodied by a control electrode of a gas-sensitive device.

A FET type gas-sensitive device according to a second embodiment of the present invention, as shown in FIGS. 1A to 1C, has a technical feature that first insulating layers 11 are formed between the control electrode 2 and the sensing material layer 6 and between the floating electrode 3 and the sensing material layer 6 in the first embodiment.

Here, FIG. 1A is a top view, FIG. 1B is a cross-sectional view taken along line A-A' of FIG. 1A and FIG. 1C is a cross-sectional view taken along line B-B'.

As shown in FIG. 1B, the gate insulating layer 9 is disposed under the floating electrode 3, the semiconductor body 12 where a channel is formed is an active region 1 surrounded by the separating insulation layer 8 and protruded on the semiconductor substrate 7.

At this time, the semiconductor body 12 is doped with impurities having the same type as the semiconductor substrate 7, but may have a different doping concentration and profile from the semiconductor substrate 7. Especially, it is preferred to be doped with impurities in order that a buried channel can be formed as mentioned above.

And it is preferable that the passivation layer 10, as shown in FIG. 1B, is formed on the top surfaces of the floating electrode 3, the control electrode 2 and the first insulating layer 11 and the sensing material layer 6 is formed to cover a part of the passivation layer 10. Here, the sentence "the sensing material layer 6 is formed to cover a part of the passivation layer 10" indicates that the sensing material layer 6 is formed on a partial or whole surface of the passivation layer 10 formed on the floating electrode 3.

By doing this, it is possible to form the sensing material layer 6, after forming the passivation layer 10, at the latter half or the last step in a fabrication process. Thus, it enables to maximally reduce the damage of the sensing material layer 6, to use a variety of sensing materials, to solve the pollution problems inducing the damage in the process and to improve the yield rate in comparison with the conventional process.

For forming the sensing material layer 6, it can be applied with one or more of the lift-off method, the shadow mask method and the inkjet printing method.

In addition, a first electrode 5, as shown in FIGS. 1A and 1B, can be formed on a side wall of the control electrode 2 and electrically connected to. The source/drain regions 13, as shown in FIGS. 1A and 1C, are electrically connected to source/drain electrodes 5a via the contacts 4.

And because the sensing material layer 6 can be formed of the same materials of the first embodiment, it enables to be operated by a mechanism of the change of the capacitance between the control electrode 2 and the floating electrode 3 or a mechanism of the generation/extinction of electric charges in the sensing material layer 6 depending on whether the predetermined gas exists or not.

In the above mentioned second embodiment, as shown in FIGS. 1A to 1C, the first insulating layer 11 is formed all of between the control electrode 2 and the floating electrode 3 and between the floating electrode 3 and the sensing material layer 6. But it can be embodied that the first insulating layer 11 is only formed any one of between the control electrode 2 and the sensing material layer 6 and between the floating electrode 3 and the sensing material layer 6.

A FET type gas-sensitive device according to a third embodiment of the present invention, as shown in FIGS. 3A to 6, has a technical feature that the first insulating layer 11 is formed one of between the control electrode 2 and the sensing material layer 6 and between the floating electrode 3 and the sensing material layer 6 in the second embodiment and that a first electrode 5 is formed the other of between the control electrode 2 and the sensing material layer 6 and between the floating electrode 3 and the sensing material layer 6.

Figure 3A:
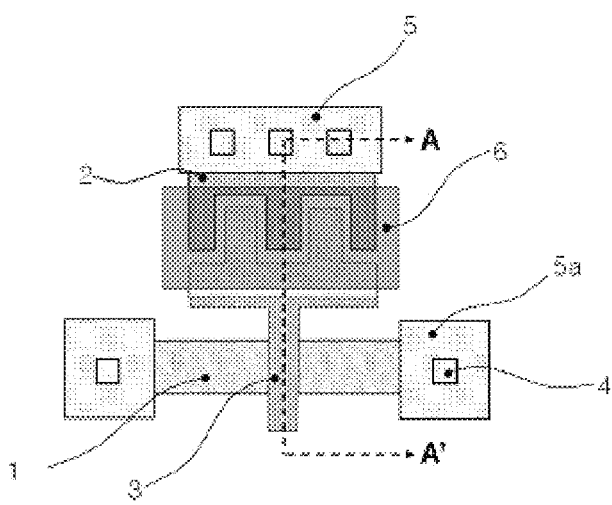
FIGS. 3A and 3B are modified views of a gas-sensitive device shown in FIG. 1A.
Figure 3B:
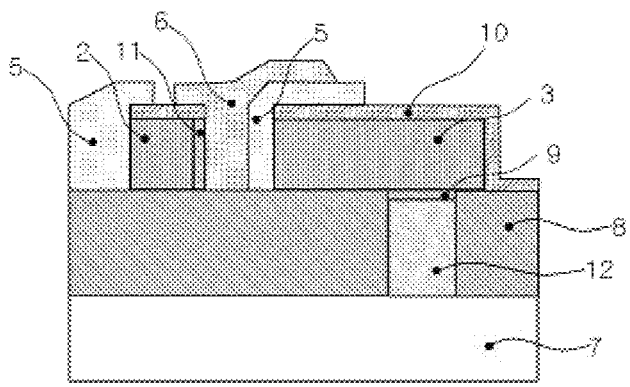
Figure 4:
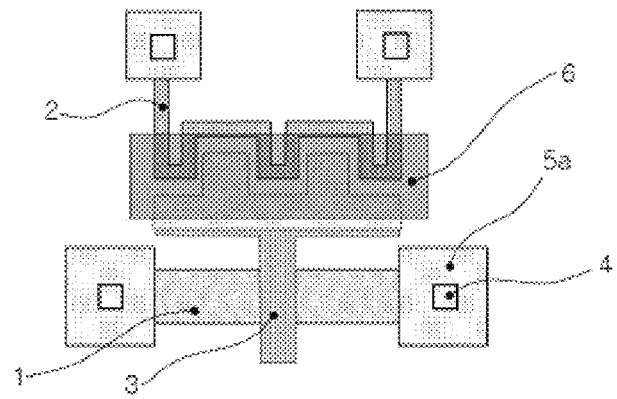
FIG. 4 is a modified view of a gas-sensitive device shown in FIG. 3A and is showing one example of a heater embodied by a control electrode of a gas-sensitive device.

In the third embodiment, as shown in FIGS. 3A to 4, when the first electrode 5 is formed between the floating electrode 3 and the sensing material layer 6, the sensing material layer 6 is electrically connected to the floating electrode 3 via the first electrode 5. Thus, when the predetermined gas being sensed, it shows an advantage that the change of the sensing material layer 6 is directly transferred to the floating electrode 3. For example, when the generation/extinction of electric changes or the change of a dielectric constant etc. happen in the sensing material layer 6 due to the predetermined gas, it induces a change of the potential of the floating electrode 3.

Figure 5A:
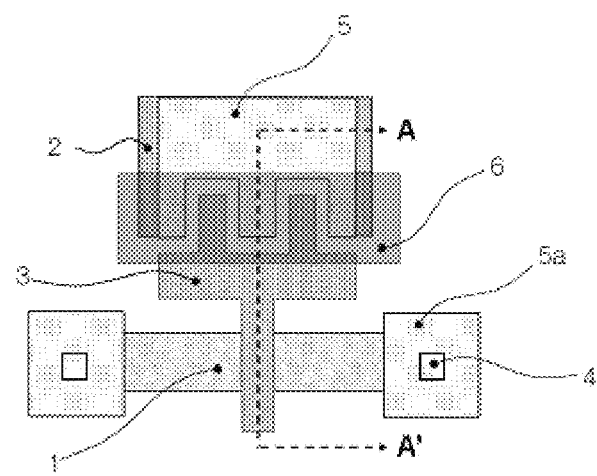
FIGS. 5A to 5C are showing a FET type gas-sensitive device having a horizontal floating gate enabling to sense the change of work function according to one embodiment of the present invention.
Figure 6:
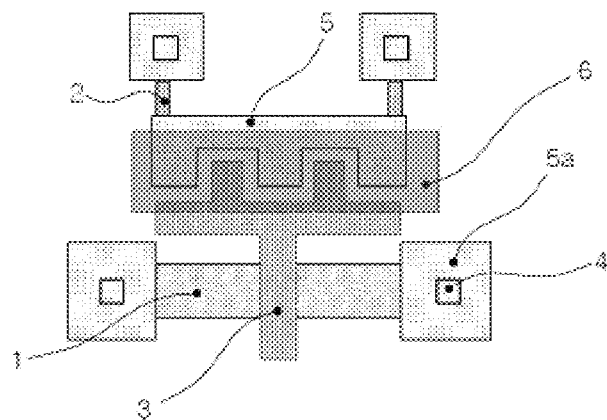
FIG. 6 is a modified view of a gas-sensitive device shown in FIG. 5A and is showing one example of a heater embodied by a control electrode of a gas-sensitive device.

On the other hand, in the third embodiment, as shown in FIGS. 5A and 6, when the first electrode 5 is formed between the control electrode 2 and the sensing material layer 6, it is used as an operating mechanism that the change of the electric potential between the control electrode 2 and the floating electrode 3 is induced by the change of the work function of the sensing material layer 6. In other words, in the above structure, when the sensing material layer 6 is formed of a material that reacts to the predetermined gas and results in a change of a work function, because the sensing material layer 6 is electrically connected to the control electrode 2 via the first electrode 5, it can induce the change of the work function of the control electrode 2. Consequently, though the same operating voltage is applied to the structure, the voltage transferred to the floating electrode 3 can be changed by depending on whether the predetermined gas exists or not. The voltage of the floating electrode 3 can be detected by sensing an electric current flowing between the source/drain electrodes 5a. Of course, in the above mentioned structure, the sensing material layer 6 can be also formed of a predetermined insulator as a material which reacts to a specific gas and results in a change of a dielectric constant or a generation or extinction of electric charges.

Figure 5B:
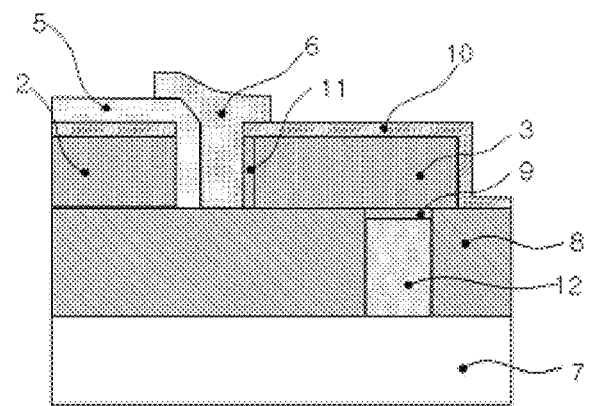

In the third embodiment, as like as the detailed description in the second embodiment, as shown in FIGS. 3B and 5B, a passivation layer 10 can be formed on the top surfaces of the floating electrode 3, the control electrode 2 and the first insulating layer 11, and the first electrode 5 can be formed to cover a part of the passivation layer 10. And the sensing material layer 6 can be formed to cover each part of the first electrode 5 and the passivation layer 10. By doing this, as the second embodiment, the sensing material layer 6 can be formed at the latter half or the last step in a fabrication process. Thus, it can have the same advantages as one mentioned in the second embodiment.

Figure 5C:
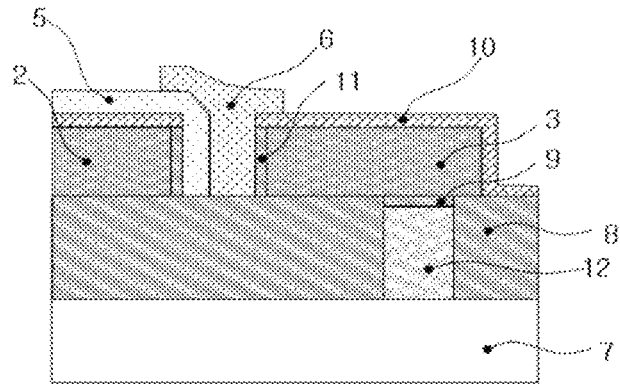

As one modification of the third embodiment, as shown in FIG. 5C, the first electrode 5 can be also formed between the first insulating layer 11 formed on the side wall of the control electrode 2 and the sensing material layer 6. In this case, it can be used as an operating mechanism that the change of the work function of the sensing material layer 6 induces the change of the electric potential between the first electrode 5 and the floating electrode 3.

As another modification of the third embodiment, not shown in the attached drawings, the first electrode 5 can be further formed between the sensing material layer 6 and the first insulating layer 11 formed on the side wall of the floating electrode 3 in FIG. 5C.

As mentioned in the second and third embodiments, it has the same advantages because the sensing material layer 6 can be formed at the latter half or the last step in a fabrication process.

And because the sensing material layer 6 can be formed of the same materials of the first embodiment, it enables to be operated by a mechanism of the change of the capacitance between the control electrode 2 and the floating electrode 3 or a mechanism of the generation/extinction of electric charges in the sensing material layer 6 depending on whether a specific gas exists or not.

Figure 9A:
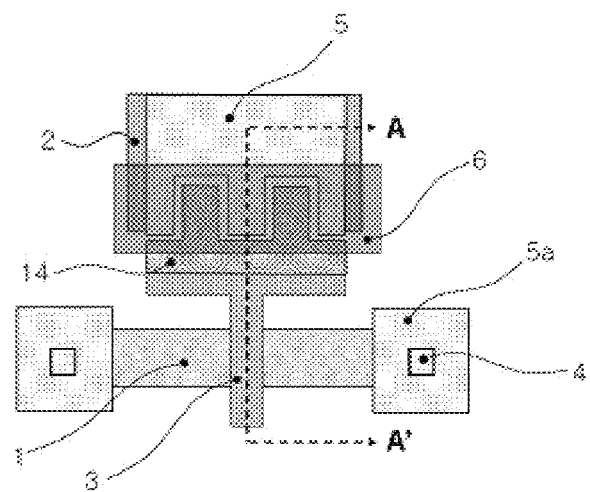
FIGS. 9A to 9E are showing a FET type gas-sensitive device having a horizontal floating gate enabling to sense the change of an electromotive force according to one embodiment of the present invention.
Figure 9B:
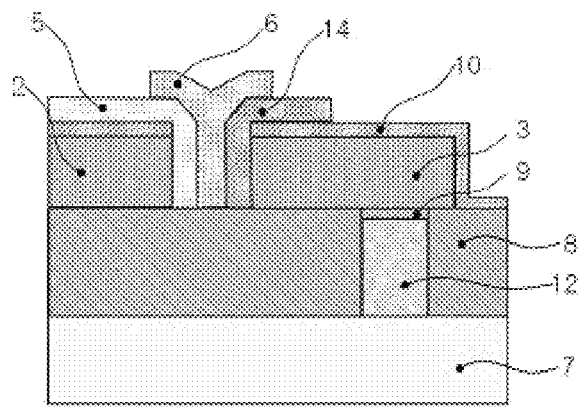
Figure 9C:
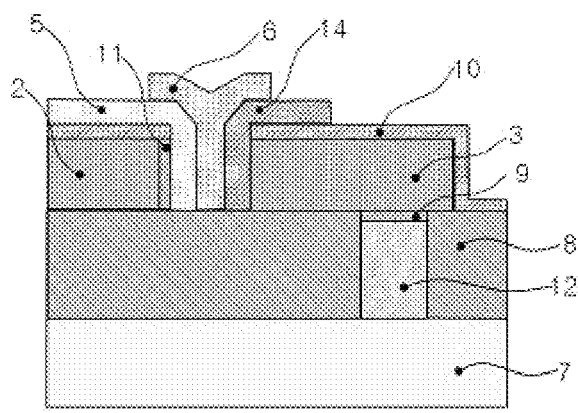
Figure 9D:
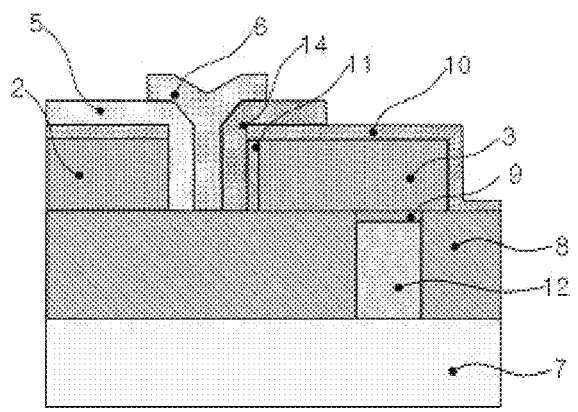
Figure 9E:
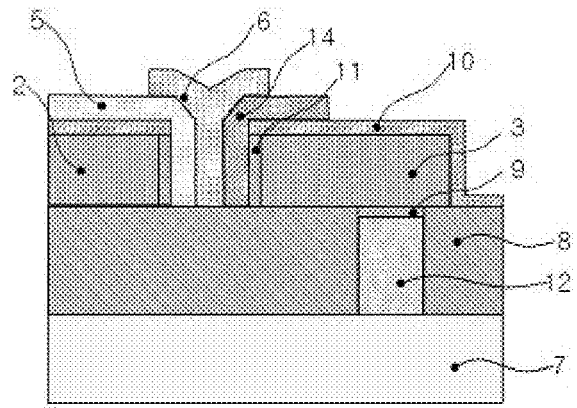
Figure 10:
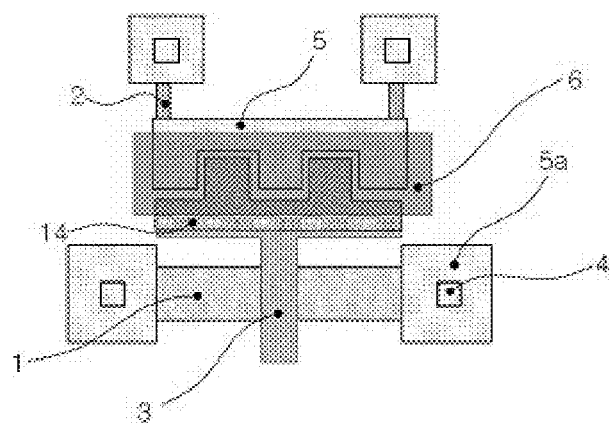
FIG. 10 is a modified view of a gas-sensitive device shown in FIG. 9A and is showing one example of a heater embodied by a control electrode of a gas-sensitive device.

A FET type gas-sensitive device according to a fourth embodiment of the present invention, as shown in FIGS. 9A to 10, has a technical feature that a first electrode 5 is formed between the control electrode 2 and the sensing material layer 6 and that a second electrode 14 is formed between the floating electrode 3 and the sensing material layer 6 in the first embodiment.

Here, the first and second electrodes 5 and 14 are preferably formed of metals that differ from each other and the sensing material layer 6 is preferably formed of a material that reacts to a predetermined gas and results in a change of an electromotive force between the first and second electrodes 5 and 14.

In detail, the first and second electrodes 5 and 14 can be formed of platinum (Pt), silver (Ag) or an alloy comprising one or more of them and the sensing material layer 6 can be formed of solid electrolyte and metal oxide etc.

By the above mentioned composition, the sensing material layer 6 reacting to a specific gas induces the change of the electromotive force between the first and second electrodes 5 and 14. The change of the electromotive force is added to the operating voltage applied to the control electrode 2 and is transferred to the floating electrode 3. The voltage of the floating electrode 3 can be detected by sensing an electric current flowing between the source/drain electrodes 5a.

And when the sensing material layer 6 is formed of an insulator, it enables to be operated by a mechanism sensing the change of the capacitance between the control electrode 2 and the floating electrode 3 induced by the change of a dielectric constant or by a mechanism sensing the generation/extinction effect of the electric charges in the sensing material layer 6 depending on whether a specific gas exists or not.

Though, in the fourth embodiment, as shown in FIG. 9B, it is possible to have a sequential structure of the first electrode 5/sensing material layer 6/second electrode 14 between the control electrode 2 and the floating electrode 3, as shown in FIGS. 9C to 9E, a first insulating layer 11 can be further formed at least one of between the control electrode 2 and the first electrode 5 and between the floating electrode 3 and the second electrode 14.

In the structures shown in FIGS. 9C and 9E, because a first insulating layer 11 is formed on at least one side wall of the control electrode 2, though the sensing material layer 6 is formed of a material that induces the change of a work function or an electromotive force, a specific gas can be sensed by an operating mechanism using the change of capacitance due to the change of a dielectric constant of the sensing material layer 6 or using the generation or extinction of electric charges in the sensing material layer 6.

In the structure shown in FIG. 9D, because a first electrode 5 is adjacently formed on the side wall of the control electrode 2, it is operated by the change of a work function or an electromotive force of the sensing material layer 6. But, when the sensing material layer 6 is formed of an insulating material, it can be also operated by the other mechanism sensing the change of capacitance due to the change of a dielectric constant or sensing the generation/extinction of electric charges.

And the fourth embodiment, as shown in FIGS. 9C to 9E, can have a structure further comprising a passivation layer 10. In this case, the passivation layer 10 is firstly formed on the top surfaces of the floating electrode 3, the control electrode 2 and the first insulating layer 11. Then the first electrode 5 is formed to cover a part of the passivation layer 10 formed on the top surface of the control electrode 2, the second electrode 14 is formed to cover a part of the passivation layer 10 formed on the top surface of the floating electrode 3, and the sensing material layer 6 is formed between the first and second electrodes 5 and 14 to cover each part of the first and second electrodes 5 and 14. By the above mentioned structure, because the sensing material layer 6 can be formed at the latter half or the last step of a fabrication process, it has the same advantages described in the second and third embodiments.

Figure 14A:
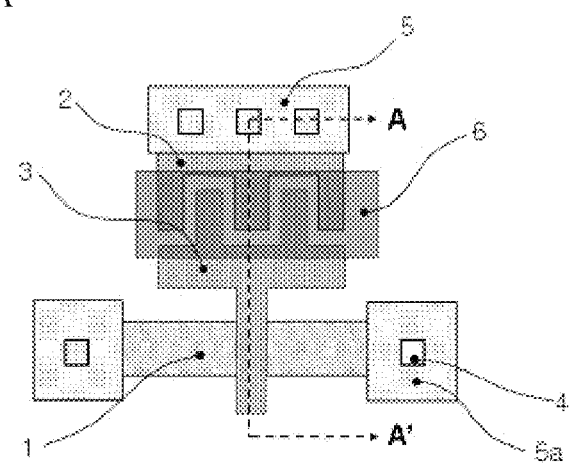
FIGS. 14A and 14B are modified views of a gas-sensitive device shown in FIG. 1A.
Figure 14B:
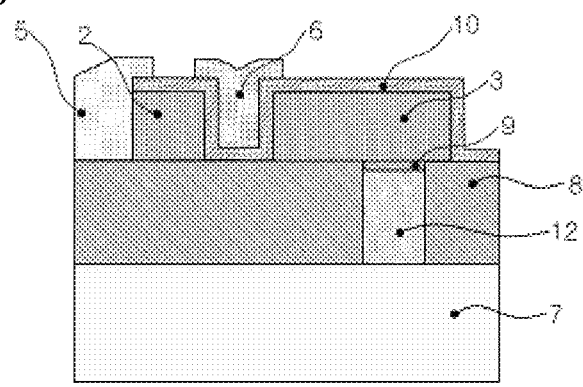

A FET type gas-sensitive device according to a fifth embodiment of the present invention, as shown in FIGS. 14A and 14B, has a technical feature that a passivation layer 10 is firstly formed on the groove formed between the control electrode 2 and the floating electrode 3 in the first embodiment and then the sensing material layer 6 is filled on the passivation layer 10.

Figure 15A:
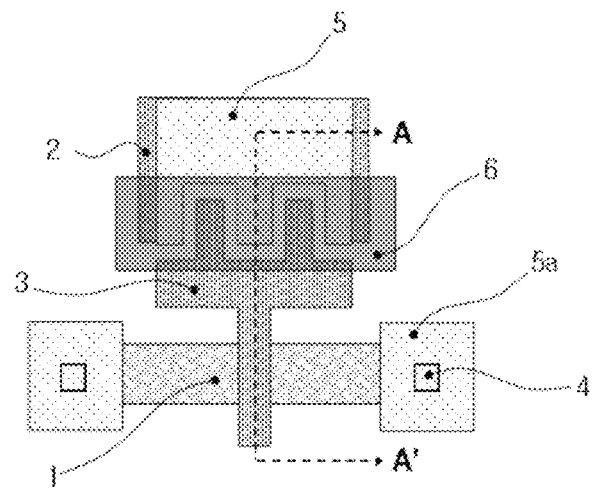
FIGS. 15A and 15B are modified views of a gas-sensitive device shown in FIG. 5A.
Figure 15B:
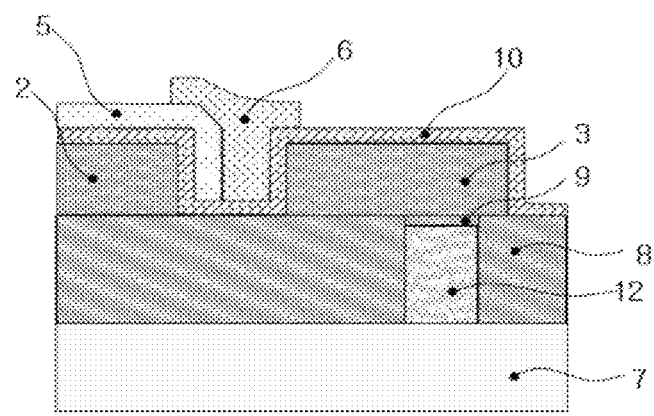

As one modification of the fifth embodiment, as shown in FIG. 15B, the sensing material layer 6 can be filled after a first electrode 5 is further formed on the passivation layer 10 formed on the groove and the surfaces of the control electrode 2 and the floating electrode 3.

Figure 16A:
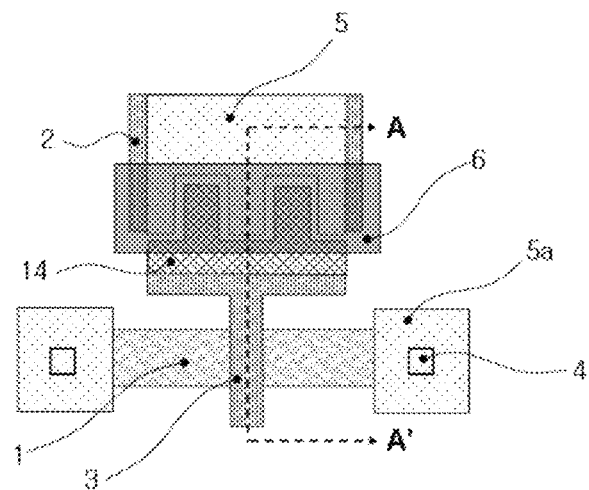
FIGS. 16A and 16B are modified views of a gas-sensitive device shown in FIG. 9A.
Figure 16B:
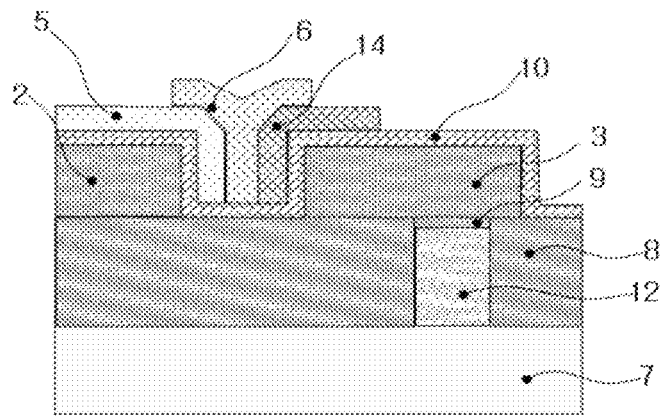

As another modification of the fifth embodiment, as shown in FIG. 16B, the sensing material layer 6 can be filled after forming the first and second electrodes 5 and 14.

As mentioned in the second to fourth embodiments, it has the same advantages because the sensing material layer 6 can be formed at the latter half or the last step in a fabrication process.

And because the sensing material layer 6 is formed of the same material as the first embodiment, it enables to be operated by a mechanism sensing the change of the capacitance between the control electrode 2 and the floating electrode 3 or by a mechanism sensing the generation/extinction effect of the electric charges depending on whether a specific gas exists or not.

In the structure shown in FIG. 15B, it can be also operated by a mechanism sensing the change of a work function. And, in the structure shown in FIG. 16B, it can be also operated by a mechanism sensing the change of an electromotive force.

Figure 17A:
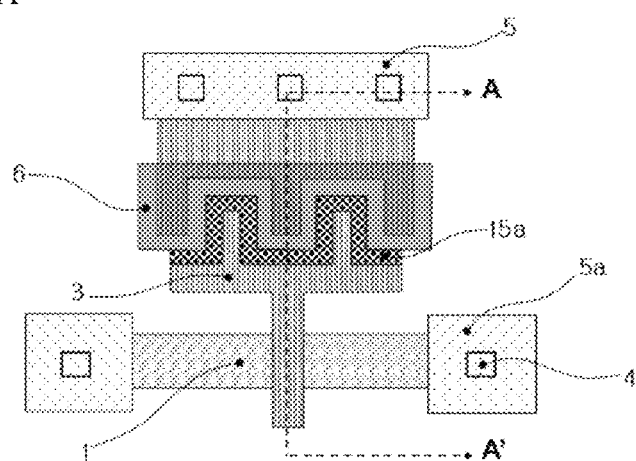
FIGS. 17A and 17B are modified views of a gas-sensitive device shown in FIG. 1A.
Figure 17B:
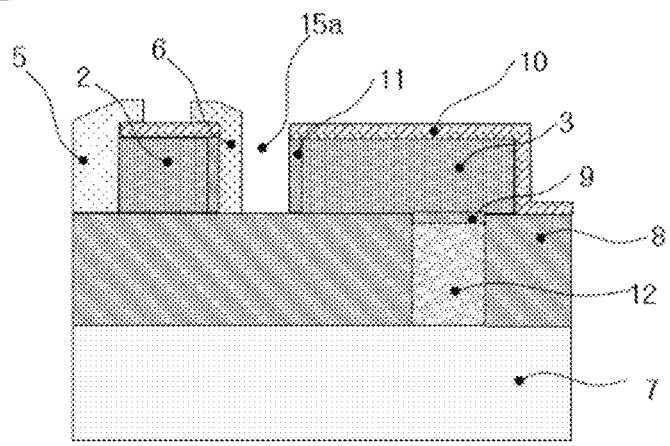
Figure 18:
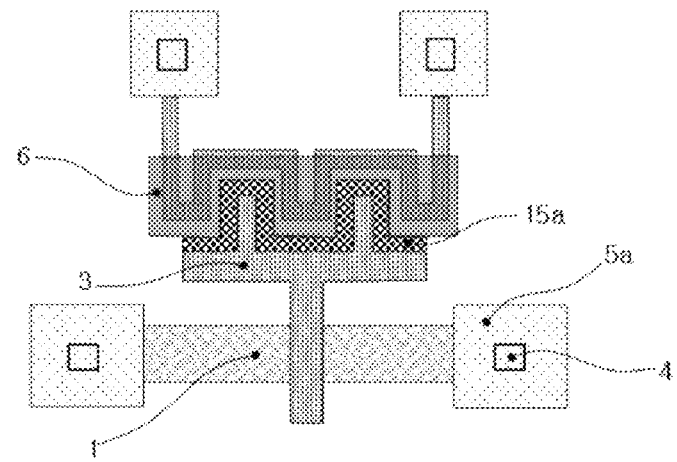
FIG. 18 is a modified view of a gas-sensitive device shown in FIG. 17A and is showing one example of a heater embodied by a control electrode of a gas-sensitive device.
Figure 19A:
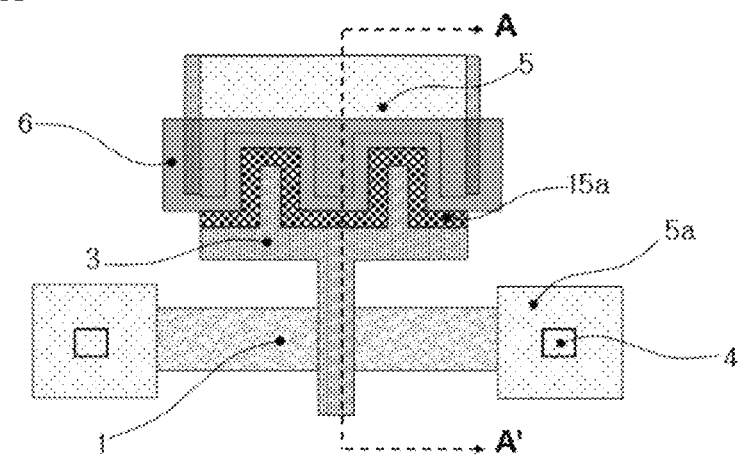
FIGS. 19A to 19C are modified views of a gas-sensitive device shown in FIG. 19A.
Figure 19B:
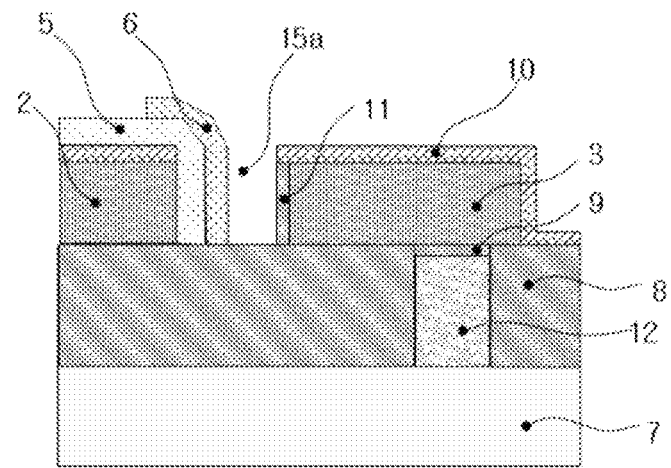
Figure 19C:
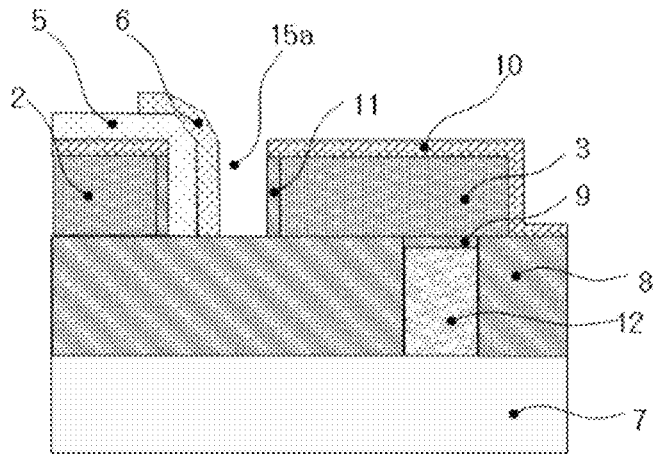
Figure 20:
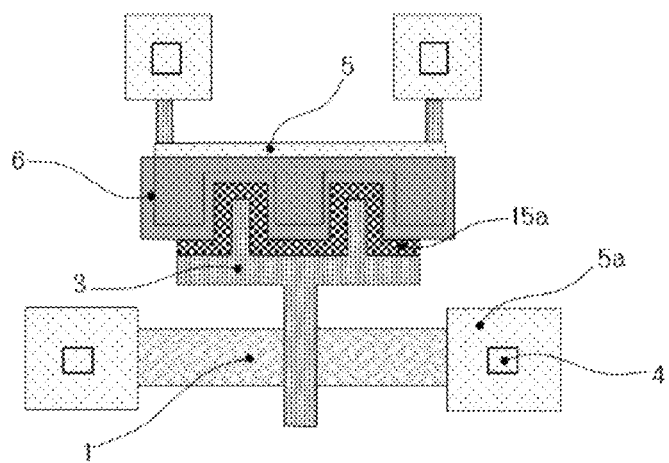
FIG. 20 is a modified view of a gas-sensitive device shown in FIG. 19A and is showing one example of a heater embodied by a control electrode of a gas-sensitive device.

A FET type gas-sensitive device according to a sixth embodiment of the present invention, as commonly shown in FIGS. 17A, 17B and 19A to 19C, has a technical feature that an air gap 15a is formed between the sensing material layer 6 and the floating electrode 3 in the first to third and fifth embodiments. In more detail, the air gap 15a is formed between the sensing material layer 6 and the first insulating layer 11 formed on the side wall of the floating electrode 3 or between the sensing material layer 6 and the passivation layer (not shown). The first insulating layer 11, as shown in FIG. 17B, or/and the first electrode 5, as shown in FIG. 19B, can be further formed between the control electrode 2 and the sensing material layer 6.

As one modification of the sixth embodiment, though it is not shown in the attached drawings, the air gap 15a can be formed between the control electrode 2 and the sensing material layer 6.

By the above mentioned structure, because a reaction gas can rapidly permeate into the air gap 15a, it enables to improve the reaction time of the device. The other features are equal to ones described in the first to fifth embodiments.

A FET type gas-sensitive device according to a seventh embodiment of the present invention, as commonly shown in FIGS. 1A to 6, 9A to 10 and 14A to 21C, has a technical feature that the floating electrode 3 has an uneven side wall facing to face with the control electrode 2 and that the control electrode 2 has an uneven side wall formed reversely to the uneven side wall of the floating electrode 3 to form an interdigitated shape with the floating electrode 3 in the first to fifth embodiments.

By the above mentioned structure, it has an advantage to raise the capacitance etc. by increasing each of areas facing between the control electrode 2 and the floating electrode 3. The other features are equal to ones described in the first to sixth embodiments.

A FET type gas-sensitive device according to an eighth embodiment of the present invention, as commonly shown in FIGS. 2, 4, 6, 10, 18, 20 and 21A, has a technical feature that the control electrode 2 further has an uneven side wall opposite to the side wall facing to face with the floating electrode 3 to form a zigzag shape in the seventh embodiment.

By the above mentioned structure, it has an advantage that the control electrode 2 can be also used as a heater by applying a voltage to both ends of the longitudinal direction of the control electrode 2. Namely, it is possible not only to sense the gas by applying a reading voltage to both ends or one end of the longitudinal direction of the control electrode 2 but also to emit the heat by applying a predetermined voltage to both ends to flow an electric current. By emitting the heat, it has advantages to induce the gas adsorption or desorption of the sensing material layer 6 and to improve the reactivity.

The reading operation and the heating operation can be operated by alternatively applying pulse type reading and heating voltages to both ends of the control electrode 2.

The control electrode 2 used as the above mentioned heater is formed of doped polysilicon, silicide, or one or more metal. The other features are equal to ones described in the first to seventh embodiments.

Figure 21A:
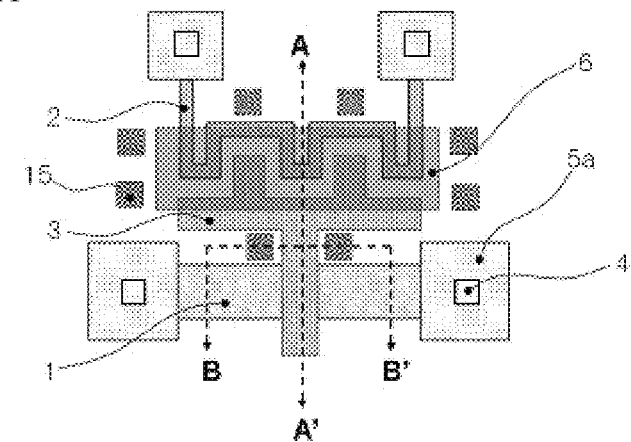
FIGS. 21A to 21C are modified views of a gas-sensitive device shown in FIG. 2.
Figure 21B:
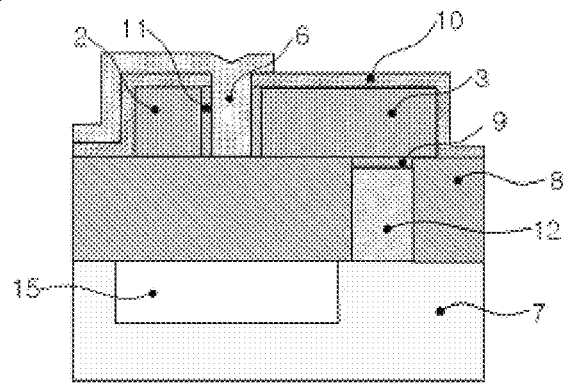
Figure 21C:
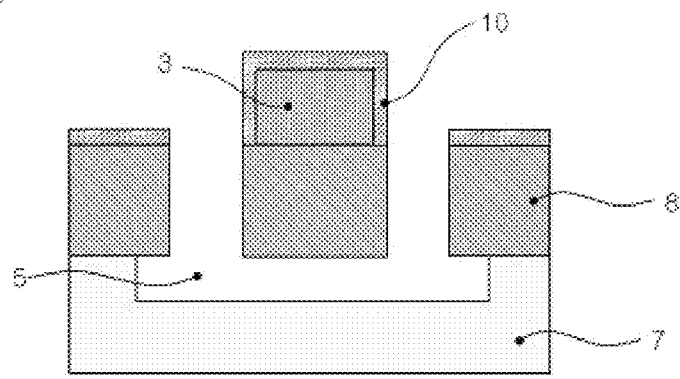

A FET type gas-sensitive device according to a ninth embodiment of the present invention, as shown in FIGS. 21A to 21C, has a technical feature that the semiconductor substrate 7 is etched with a predetermined depth to form an air layer 15 under the control electrode 2 and the sensing material layer 6 in the eighth embodiment.

As mentioned above, by forming the air layer 15 under the control electrode 2 and the sensing material layer 6, it has an advantage to efficiently transfer the heat emitted from the control electrode 2 operating as the heater into the sensing material layer 6 by cutting off the heat loss through the semiconductor substrate 7 with a high thermal conduction.

The air layer 15, as shown in FIG. 21C, is preferably extended to the semiconductor substrate 7 located under a part of the floating electrode 3. In this case, it has advantages to vastly reduce the above mentioned heat loss and to increase the coupling ratio between the control electrode 2 and the floating electrode 3 by reducing parasite capacitance components between the semiconductor substrate 7 and the floating electrode 3.

And the air layer 15, as shown in FIG. 21, can be formed by a selective isotropic etching after forming a plurality of through-holes on a separating insulation layer 8 to wrap around the air layer forming portions and to expose the semiconductor substrate 7.

The other features are equal to ones described in the first to eighth embodiments.

A FET type gas-sensitive device according to a tenth embodiment of the present invention, as commonly shown in FIGS. 7A to 8 and 11A to 13, can be comprised of: a semiconductor substrate 7; a semiconductor body 12 formed to be protruded on the semiconductor substrate 7; a separating insulation layer 8 formed on a side wall of the semiconductor body 12 and on the semiconductor substrate 7; a gate insulating layer 9 formed on the semiconductor body 12; a floating electrode 3 formed on the gate insulating layer 9 and on the separating insulation layer 8; a passivation layer 10 formed on the floating electrode 3 and on the separating insulation layer 8; a first electrode 5 formed on the passivation layer 10 to be face to face with and to be horizontally separated from at least one side wall of the floating electrode 3; a sensing material layer 6 formed on the passivation layer 10 between the first electrode 5 and the floating electrode 3; and source/drain regions 13 formed in the semiconductor body 12 at the both sides of the floating electrode 3.

Here, the semiconductor body 12 is preferably doped with impurities in order that a buried channel can be formed inside and at a little distance from the surface of the semiconductor body 12 through controlling an impurity type, a doping concentration and a doping profile etc. By the buried channel, it is possible to reduce a noise of the device to increase the signal-to-noise ratio (SNR) which is a very important factor of the gas-sensitive sensor.

The first electrode 5 plays a role of the control electrode 2 in the first to eighth embodiments and can be formed of one or more of impurity-doped polysilicon, polysilicon germanium, silicide, metal, conductive metal oxide and conductive nitride.

And the sensing material layer 6 can be directly filled between the control electrode 2 and the passivation layer 10 formed on the side wall of the floating electrode 3 being face to face with and horizontally separated from each other or, as the below mentioned embodiments, can be filled on an extra insulating or conductive material firstly interposed between them.

Particularly, if the sensing material layer 6 is formed of a material that reacts to a predetermined gas and results in a change of a dielectric constant or a generation or extinction of electric charges, it enables to be operated by a mechanism sensing the change of a capacitance or the generation/extinction of electric charges.

Figure 7A:
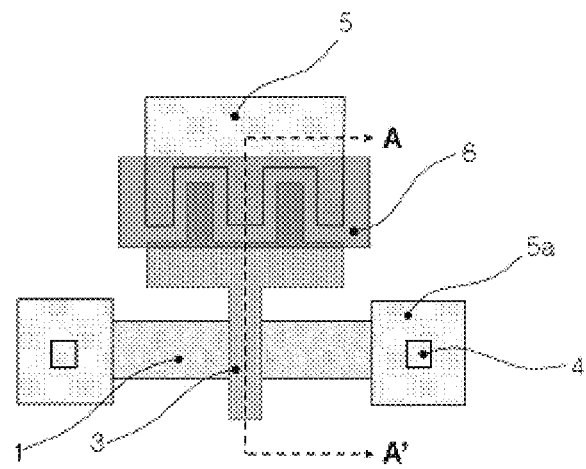
FIGS. 7A and 7B are showing a FET type gas-sensitive device having a horizontal floating gate enabling to sense the change of capacitance or the generation/extinction of electric charges according to one embodiment of the present invention.
Figure 7B:
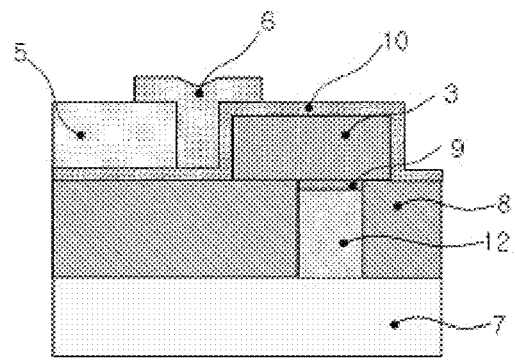

Furthermore, as FIG. 7B, in the structure of the first electrode 5 directly contacted to the sensing material layer 6, it enables to be operated by a mechanism sensing the change of a work function depending on the material of the sensing material layer 6.

And in the composition of the tenth embodiment, because the first electrode 5, the floating electrode 3 and the sensing material layer 6 are basically formed in a horizontal direction as the first embodiment, it enables to solve the problems of the conventional vertical type gas-sensitive device.

A FET type gas-sensitive device according to a eleventh embodiment of the present invention, as shown in FIGS. 11A to 13, has a technical feature that a second electrode 14 is formed between the passivation layer 10 on the side wall of the floating electrode 3 and the sensing material layer 6 in the tenth embodiment.

Here, the first and second electrodes 5 and 14 are preferably formed of metals which differ from each other and the sensing material layer 6 is preferably formed of a material that reacts to a specific gas and results in the change of an electromotive force between the first and second electrodes 5 and 14.

In detail, the first and second electrodes 5 and 14 can be formed of platinum (Pt), silver (Ag) or an alloy comprising one or more of them and the sensing material layer 6 can be formed of solid electrolyte and metal oxide etc.

By the above mentioned composition, it enables to be operated by a mechanism sensing the change of an electromotive force depending on a specific gas through the sensing material layer 6.

Of course, when the sensing material layer 6 is formed of an insulator, it enables to be operated by a mechanism sensing the change of the capacitance or the generation/extinction of electric charges. And when the sensing material layer 6 is formed of conductive materials, it enables to be operated by a mechanism sensing the change of a work function.

Figure 11A:
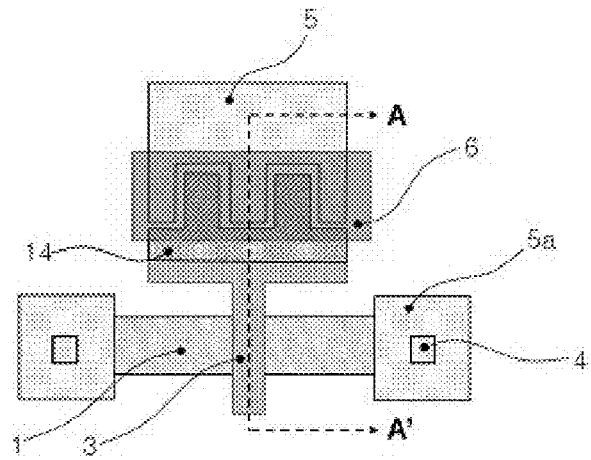
FIGS. 11A and 11B are structurally modified views of FIGS. 7A and 7B, respectively, but the operating mechanism is to sense the change of an electromotive force as like as FIGS. 9A to 9E.
Figure 11B:
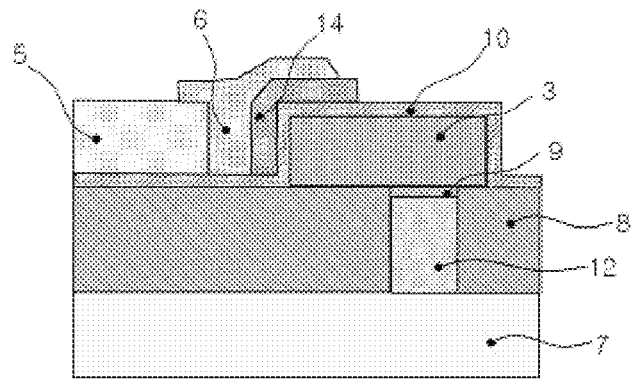

And, as shown in FIG. 11B, it is preferred to form a structure that comprises a second electrode 14 formed on the side wall and the partial top surface of the floating electrode 3 interlaying the passivation layer 10 and facing to face with the first electrode 5. The sensing material layer 6 is preferred to be filled in a groove on the passivation layer 10 between the first and second electrodes 5 and 14. By this structure, because the sensing material layer 6 can be formed at the latter half or the last step of a fabrication process, it has the same advantages described in the above mentioned embodiments.

Figure 12A:
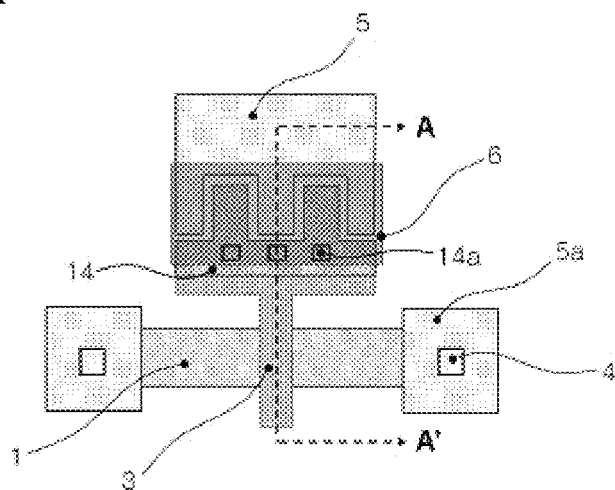
FIGS. 12A and 12B are modified views of a gas-sensitive device shown in FIG. 11A.
Figure 12B:
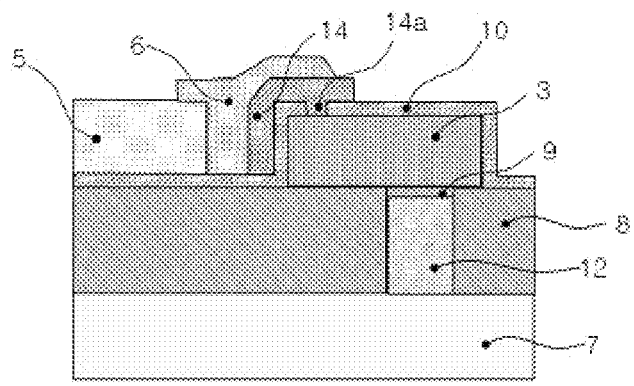

FIGS. 12A and 12B are showing that the second electrode 14 can be electrically connected to the floating electrode 3 via contacts 14a formed on the passivation layer 10 in the structures shown in FIGS. 11A and 11B. By doing this, it has an advantage to improve a coupling ratio between the first electrode 5 and the floating electrode 3.

A FET type gas-sensitive device according to a twelfth embodiment of the present invention has a technical feature that an air gap (not shown) is formed between the sensing material layer 6 and the floating electrode 3 covered with the passivation layer 10 in the tenth embodiment.

As one modification of the twelfth embodiment, the air gap (not shown) can be formed between the first electrode 5 and the opposite side of sensing material layer 6.

And a first insulating layer 11 can be further formed between the first electrode 5 and the opposite side of the sensing material layer 6 formed of the air gap (in the former embodiment) or between the sensing material layer 6 and the floating electrode 3 covered with the passivation layer 10 (in the latter embodiment).

By the above mentioned structure, because the reaction gas can rapidly permeate into the air layer (not shown), it enables to improve the reaction time of the device. The other features are equal to ones described in the tenth embodiment.

A FET type gas-sensitive device according to a thirteenth embodiment of the present invention, as commonly shown in FIGS. 7A to 8 and 11A to 13, has a technical feature that the floating electrode 3 has an uneven side wall facing to face with the first electrode 5 and the first electrode 5 has an uneven side wall formed reversely to the uneven side wall of the floating electrode 3 to form an interdigitated shape with the floating electrode 3 in the tenth and eleventh embodiments.

By the above mentioned structure, it has an advantage to raise the capacitance etc. by increasing each of areas facing between the first electrode 5 and the floating electrode 3. The other features are equal to ones described in the tenth and eleventh embodiments.

Figure 8:
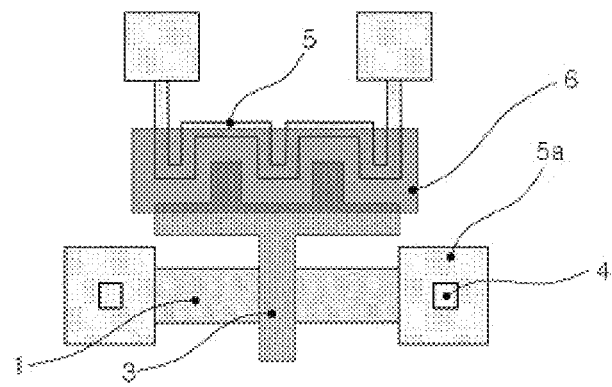
FIG. 8 is a modified view of a gas-sensitive device shown in FIG. 7A and is showing one example of a heater embodied by a control electrode of a gas-sensitive device.
Figure 13:
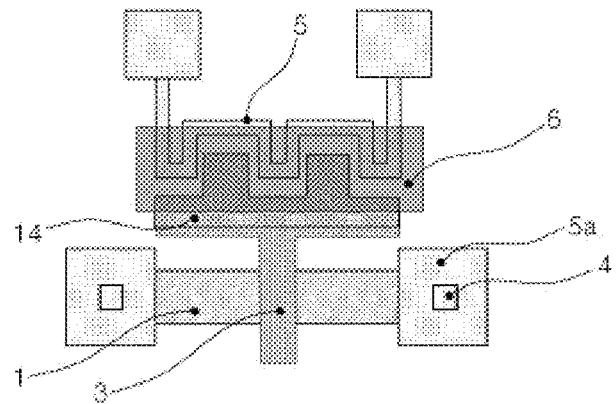
FIG. 13 is a modified view of a gas-sensitive device shown in FIG. 11A and is showing one example of a heater embodied by a control electrode of a gas-sensitive device.

A FET type gas-sensitive device according to a fourteenth embodiment of the present invention, as commonly shown in FIGS. 8 and 13, has a technical feature that the first electrode 5 further has an uneven side wall opposite to the side wall facing to face with the floating electrode 3 to form a zigzag shape in the thirteenth embodiment.

By the above mentioned structure, it has an advantage that the first electrode 5 can be also used as a heater by applying a voltage to both ends of the longitudinal direction of the first electrode 5. Namely, it is possible not only to sense the gas by applying a reading voltage to both ends or one end of the longitudinal direction of the first electrode 5 but also to emit the heat by applying a predetermined voltage to both ends to flow an electric current. By emitting the heat, it has advantages to induce the gas adsorption or desorption of the sensing material layer 6 and to improve the reactivity.

The reading operation and the heating operation can be operated by alternatively applying pulse type reading and heating voltages to both ends of the first electrode 5.

The first electrode 5 used as the above mentioned heater is formed of doped polysilicon, silicide, or one or more metal. The other features are equal to ones described in the tenth to thirteenth embodiments.

A FET type gas-sensitive device according to an fifteenth embodiment of the present invention has a technical feature that the semiconductor substrate 7 is etched with a predetermined depth to form an air layer (not shown) under the first electrode 5 and the sensing material layer 6 in the fourteen embodiment.

As mentioned above, by forming the air layer under the first electrode 5 and the sensing material layer 6, it has advantage to efficiently transfer the heat emitted from the first electrode 5 operating as the heater into the sensing material layer 6 by cutting off the heat loss through the semiconductor substrate 7 with a high thermal conduction.

The air layer is preferably extended to the semiconductor substrate 7 located under a part of the floating electrode 3. In this case, it has advantages to vastly reduce the above mentioned heat loss and to increase the coupling ratio between the first electrode 5 and the floating electrode 3 by reducing parasite capacitance components between the semiconductor substrate 7 and the floating electrode 3.

And the air layer can be formed by a selective isotropic etching after forming a plurality of through-holes on a separating insulation layer 8 to wrap around the air layer forming portions and to expose the semiconductor substrate 7.

The other features are equal to ones described in the tenth to fourteenth embodiments.

A FET type gas-sensitive device array according to a sixteenth embodiment of the present invention has a technical feature that a plurality of gas-sensitive devices are arrayed in a semiconductor substrate for sensing two or more different kinds of gases, wherein the plurality of gas-sensitive devices comprise two or more gas-sensitive devices having different operation mechanisms due to a different structure or sensing material, and each of the gas-sensitive devices is the FET type gas-sensitive device according to one of the first to thirteenth embodiments.

The FET-type gas-sensitive devices according to the first to fifteenth embodiments, as in detail mentioned above, basically have a different cross-sectional structure of the device and/or a different operating mechanism depending on whether a control electrode 2 or a first electrode 5 is face to face with and horizontally separated from at least one side wall of the floating electrode 3 and a sensing material layer 6 is formed to cover the separated space (groove) and whether one or more of a first insulating layer 11, a first electrode 5, a second electrode 14 and a passivation layer 10 are further formed to contact to the sensing material layer 6 or not in the groove.

Namely, although the sensing material layer 6 is formed of the same material, if the cross-sectional structures (e.g., ones taken along A-A' line of accompanying drawings) of the FET type gas-sensitive devices according to the first to fifteenth embodiments are different, the kinds of reacting gases can be different due to the difference of the operating mechanism depending on the cross-sectional structure.

Reversely, although the cross-sectional structures of the FET type gas-sensitive devices according to the first to fifteenth embodiments are the same, if the sensing material layers 6 are formed of materials different each other, the kinds of reacting gases can also be different due to the difference of the operating mechanism depending on the sensing material.

Thus, by using the above mentioned characteristics, the gas-sensitive device array according to the sixteenth embodiment can be arrayed with two or more FET type gas-sensitive devices according to the first to fifteenth embodiments in one semiconductor, which have the operating mechanisms different each other due to the difference of the cross-sectional structure or the sensing material.

Figure 22:
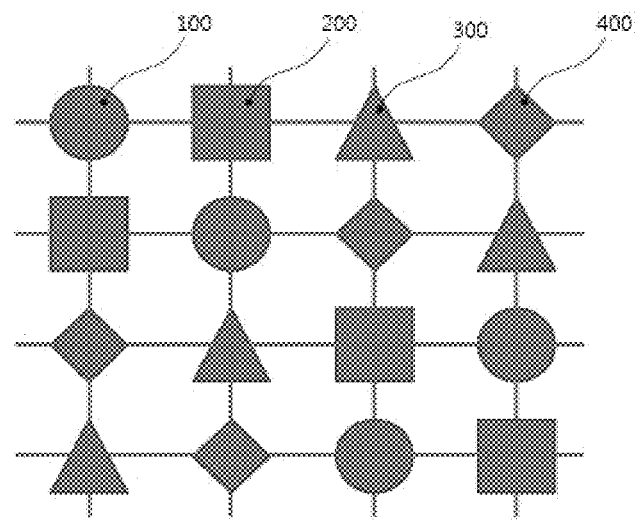
FIG. 22 is an equivalent diagram showing one example of a gas-sensitive array embodied with a plurality of gas-sensitive devices operated by four kinds of sensing mechanisms according to the present invention.

A FET type gas-sensitive device array according to a seventeenth embodiment of the present invention, as shown in FIG. 22, has a technical feature that the plurality of gas-sensitive devices comprise gas-sensitive devices having two or more different operation mechanisms of the dielectric constant change, the generation or extinction of electric charges, the work function change and the electromotive force change of the sensing material layer in the sixteenth embodiment regarding a gas-sensitive device array.

In FIG. 22, the reference number 100 indicates a gas-sensitive device sensing the change of capacitance by the change of a dielectric constant of the sensing material layer 6, 200 indicates a gas-sensitive device sensing the generation/extinction of electric charges of the sensing material layer 6, 300 indicates a gas-sensitive device sensing the change of a work function of the sensing material layer 6 and 400 indicates a gas-sensitive device sensing the change of an electromotive force of the sensing material layer 6.

Because the four sensing mechanisms respectively show the different sensing characteristics (it is called a sensing fingerprint) to a specific gas though using the same sensing material layer 6, it has an advantage to precisely sense the kinds and concentration of gases without using several different sensing materials.

In the above mentioned FET type gas-sensitive device according to each of embodiments of the present invention, when the sensing material layer 6 and the control electrode 2 are removed and the floating electrode 3 is used as a gate electrode, it becomes a general switching device as a MOSFET. Thus, the MOSFETs can be integrated together with the FET type gas-sensitive device mentioned above each embodiment in the same substrate. In this case, the MOSFETs can be used to embody the peripheral circuits of the gas-sensitive device.

The FET type gas-sensitive device having a horizontal floating gate according to the present invention can be embodied by a simple fabrication process and be easily fabricated by the compatible conventional CMOS process. Thus, it has a high industrial applicability. Especially, in comparison with the up-to-date developed sensors (refer to Patent document 2) in the industry, the present invention enables to be with excellent performance, to reduce fabrication cost and to have extremely high applicability to a chemical sensor and a biosensor etc.

What is claimed is:

1. A FET type gas-sensitive device, comprising:
   a semiconductor substrate;
   a semiconductor body protruded on the semiconductor substrate;
   a separating insulation layer formed on a side wall of the semiconductor body and on the semiconductor substrate;
   a gate insulating layer formed on the semiconductor body;
   a floating electrode formed on the gate insulating layer and on the separating insulation layer;
   a control electrode formed on the separating insulation layer to be face to face with and to be horizontally separated from at least one side wall of the floating electrode formed on the separating insulation layer;
a sensing material layer formed between the control electrode and the floating electrode; and
source/drain regions formed in the semiconductor body at the both sides of the floating electrode,
wherein at least part of the sensing material is disposed on and in between opposed vertical sidewalls of the control electrode and the floating electrodes and on the separating insulation layer, and
wherein the separating insulation layer is thicker than the gate insulating layer.

2. The FET type gas-sensitive device of claim 1,
wherein a first insulating layer is formed at least one of between the control electrode and the sensing material layer and between the floating electrode and the sensing material layer.

3. The FET type gas-sensitive device of claim 2,
wherein a passivation layer is formed on the top surfaces of the floating electrode, the control electrode and the first insulating layer, and
wherein the sensing material layer is formed to cover a part of the passivation layer.

4. The FET type gas-sensitive device of claim 2,
wherein the first insulating layer is formed one of between the control electrode and the sensing material layer and between the floating electrode and the sensing material layer, and
wherein a first electrode is formed the other of between the control electrode and the sensing material layer and between the floating electrode and the sensing material layer.

5. The FET type gas-sensitive device of claim 4,
wherein a passivation layer is formed on the top surfaces of the floating electrode, the control electrode and the first insulating layer,
wherein the first electrode is formed to cover a part of the passivation layer, and
wherein the sensing material layer is formed to cover each part of the first electrode and the passivation layer.

6. The FET type gas-sensitive device of claim 4,
wherein the first electrode is formed between the control electrode and the sensing material layer, and
wherein the sensing material layer is formed of a material that reacts to a predetermined gas and results in a change of a work function of the control electrode or a change of a dielectric constant or a generation or extinction of electric charges.

7. The FET type gas-sensitive device of claim 1,
wherein a first electrode is formed between the control electrode and the sensing material layer, and
wherein a second electrode is formed between the floating electrode and the sensing material layer.

8. The FET type gas-sensitive device of claim 7,
wherein a first insulating layer is formed at least one of between the control electrode and the first electrode and between the floating electrode and the second electrode.

9. The FET type gas-sensitive device of claim 8,
wherein a passivation layer is formed on the top surfaces of the floating electrode, the control electrode and the first insulating layer,
wherein the first electrode is formed to cover a part of the passivation layer formed on the top surface of the control electrode,
wherein the second electrode is formed to cover a part of the passivation layer formed on the top surface of the floating electrode, and
wherein the sensing material layer is formed between the first electrode and the second electrode to cover each part of the first electrode and the second electrode.

10. The FET type gas-sensitive device of claim 8,
wherein the first and second electrodes are formed of metals different from each other, and
wherein the sensing material layer is formed of a material that reacts to a predetermined gas and results in a change of an electromotive force between the first and second electrodes or a change of a dielectric constant or a generation or extinction of electric charges.

11. The FET type gas-sensitive device of claim 1,
wherein the sensing material layer is formed on a passivation layer formed on the surface of a groove between the control electrode and the floating electrode.

12. The FET type gas-sensitive device of claim 11,
wherein a first electrode is formed on the passivation layer between the control electrode and the sensing material layer.

13. The FET type gas-sensitive device of claim 12,
wherein a second electrode is formed on the passivation layer between the floating electrode and the sensing material layer.

14. The FET type gas-sensitive device of claim 1,
wherein the semiconductor body is doped with impurities to form a buried channel,
wherein the control electrode is formed of one or more materials of polysilicon, polysilicon germanium, silicide, metal, conductive metal oxide and conductive nitride, and
wherein the sensing material layer is formed of a material that reacts to a predetermined gas and results in a change of a dielectric constant or a generation or extinction of electric charges.

15. The FET type gas-sensitive device of claim 1,
wherein an air gap is formed between the control electrode and the sensing material layer or between the sensing material layer and the floating electrode.

16. The FET type gas-sensitive device of claim 15,
wherein the air gap is formed between the sensing material layer and the floating electrode, and
wherein at least one of a first insulating layer and a first electrode are further formed between the control electrode and the sensing material layer.

17. The FET type gas-sensitive device of claim 1,
wherein the floating electrode has an uneven side wall facing to face with the control electrode, and
wherein the control electrode has an uneven side wall formed reversely to the uneven side wall of the floating electrode to form an interdigitated shape with the floating electrode.

18. The FET type gas-sensitive device of claim 17,
wherein the control electrode further has an uneven side wall opposite to the side wall facing to face with the floating electrode to form a zigzag shape and is used as a heater.

19. The FET type gas-sensitive device of claim 18,
wherein the semiconductor substrate is etched with a predetermined depth to form an air layer under the control electrode and the sensing material layer.

20. The FET type gas-sensitive device of claim 19, wherein the air layer is extended to the semiconductor substrate located under a part of the floating electrode.

* * * * *